United States Patent [19]

Spindel et al.

[11] Patent Number: 5,436,137
[45] Date of Patent: Jul. 25, 1995

[54] DNA SEQUENCE WHICH ENCODES A PEPTIDE CAPABLE OF PROMOTING ACROSOME REACTION

[75] Inventors: Eliot R. Spindel, Oswego; Srinivasan Vijayaraghavan, Beaverton; Srinivasa R. Nagalla, Portland; Kang Li, Hillsboro, all of Oreg.

[73] Assignee: Oregon Regional Primate Research Center, Beaverton, Oreg.

[21] Appl. No.: 39,778

[22] Filed: Mar. 23, 1993

Related U.S. Application Data

[63] Continuation-in-part of Ser. No. 919,731, Jul. 27, 1992, abandoned.

[51] Int. Cl.⁶ .................. C12P 21/06; C12N 9/48; A61K 7/46; C07H 19/00
[52] U.S. Cl. .................. 435/69.1; 435/240.2; 435/252.3; 435/320.1; 435/212; 424/94.63; 514/2; 514/12; 536/22.1; 536/23.1; 536/23.2; 536/23.5
[58] Field of Search .................. 424/94.63; 435/212, 435/69.1, 240.2, 252.3, 320.1; 514/2, 12; 536/22.1, 23.1, 23.2, 23.5

[56] References Cited

PUBLICATIONS

Nagalla et al. "Bombesin-like . . ." 22nd Meeting SR for Neurosci Oct. 25–30, 1992.
Gavessi et al. "Isolation oat alumina". . . Fert. Steril. 51(6) pp. 1034–1039 1989.
Glover Gene donig pp. 1–21 1984.
Naylor et al. "Human Gastrin . . ." Som Cell J Mol Gen 13(1) pp. 87–91 1987.
Nagalla et al. "Gastron–uleasy peptide", JBC 267(10) pp. 6916–6922 Apr. 5, 1992.
Wasanwar "Enryl events . . ." Ann. Rev. Cell Biol. 1987 3:109–142 1989.

Primary Examiner—Robert A. Wax
Assistant Examiner—Hyosuk Kim
Attorney, Agent, or Firm—Fish & Richardson

[57] ABSTRACT

A pure DNA encoding a peptide which is capable of promoting acrosome reaction and the encoded peptide. Also disclosed are a vector and a cell containing such a DNA, a pharmaceutical composition which includes such a peptide, a method of promoting fertilization using such a peptide, and a method of preparing such a peptide by recombinant technology.

24 Claims, 4 Drawing Sheets

GGCAACTCTA GAGGGGTGTG TATGTGGCAG TTCAGGGACA GTTTGAGCTT TCGGGTAGAG

GCAGCCTAGG GAAACCGGCA TAAAGCAGTT TCTTTCTCTA TTCCATGGAA GCTGC

ATG CTT GTG AAA AGG GCC AGG TGT CTT CTG TCT TGC CAT GCA AGT GGG
Met Leu Val Lys Arg Ala Arg Cys Leu Leu Ser Cys His Ala Ser Gly

CAG GGC TGC TTG GGA ATA CCA GGG CAC TTA ATG GGG AAA AAG AGC ACA
Gln Gly Cys Leu Gly Ile Pro Gly His Leu Met Gly Lys Lys Ser Thr

GGG GAG TCT TCT GTT TCT GAG AGA GGG AGC CTA AAG CAG CAG CTG AGA
Gly Glu Ser Ser Val Ser Glu Arg Gly Ser Leu Lys Gln Gln Leu Arg

GAG TAC ATC AGG TGG GAA GAA GCT GCA AGC AAT TTG CTG GGT CTC ATA
Glu Tyr Ile Arg Trp Glu Glu Ala Ala Ser Asn Leu Leu Gly Leu Ile

GAA GCA AAG GAG AAC AGA AAC CAC CAG CCA CCT CAA CCC AAG GCC CTG
Glu Ala Lys Glu Asn Arg Asn His Gln Pro Pro Gln Pro Lys Ala Leu

GGC AAT CAG CAG CCT TCG TGG GAT TCA GAG GAT AGC AGC AAC TTC AAA
Gly Asn Gln Gln Pro Ser Trp Asp Ser Glu Asp Ser Ser Asn Phe Lys

GAT GTA GGT TCA AAA GGC AAA GTT GGT AGA CTC TCT GCT CCA GGT TCT
Asp Val Gly Ser Lys Gly Lys Val Gly Arg Leu Ser Ala Pro Gly Ser

CAA CGT GAA GGA AGG AAC CCC CCA GCT GAA CCA GCA ATG ACA ATG ATG
Gln Arg Glu Gly Arg Asn Pro Pro Ala Glu Pro Ala Met Thr Met Ala

GCC TCT CTC AAA GGA GAA AAA CAA AAC CCG TAA GAGACTGCGT TCTGCAAGCA
Ala Ser Leu Lys Gly Glu Lys Gln Asn Pro

TCAGTTCTAC GGATCATCAA CAAGATTTCC TTGTGCAAAA TATTTGACTA TTCTTGTATC

TTTCATCCTT GACTAAATTC GTGATTTTCA AGC (SEQ ID NO: 13)

FIG. 1

AGCAACTCTA GAGGGGTGTG TATGTGGCAG TTTAGGGACA GTTTGAGCTT TCAGGTAGAG

GCAGCCTAGG GAAACTGGCA TAAAGCAGTT TCTTTCTCTA TTCCATGGAA GTTGC

| ATG | CTT | GTG | AAA | AGG | GCC | AGC | TAT | CTT | CTG | TCT | TGC | CAT | ACA | AGT | GGG |
|-----|-----|-----|-----|-----|-----|-----|-----|-----|-----|-----|-----|-----|-----|-----|-----|
| Met | Leu | Val | Lys | Arg | Ala | Ser | Tyr | Leu | Leu | Ser | Cys | His | Thr | Ser | Gly |

| CAG | AGC | TGC | CTG | GGA | ATA | CCA | GGG | CAC | TTA | ATG | GGG | AAA | AAG | AGC | ACA |
|-----|-----|-----|-----|-----|-----|-----|-----|-----|-----|-----|-----|-----|-----|-----|-----|
| Gln | Ser | Cys | Leu | Gly | Ile | Pro | Gly | His | Leu | Met | Gly | Lys | Lys | Ser | Thr |

| GGG | GAG | TCT | TCT | TCT | GTT | TCT | GAG | AGA | GGG | AGC | CTG | AAG | CAG | CAG | CTG |
|-----|-----|-----|-----|-----|-----|-----|-----|-----|-----|-----|-----|-----|-----|-----|-----|
| Gly | Glu | Ser | Ser | Ser | Val | Ser | Glu | Arg | Gly | Ser | Leu | Lys | Gln | Gln | Leu |

| AGA | GAG | TAC | ATC | AGG | TGG | GAA | GAA | GCT | GCA | AGG | AAT | TTG | CTG | GGT | CTC |
|-----|-----|-----|-----|-----|-----|-----|-----|-----|-----|-----|-----|-----|-----|-----|-----|
| Arg | Glu | Tyr | Ile | Arg | Trp | Glu | Glu | Ala | Ala | Arg | Asn | Leu | Leu | Gly | Leu |

| ATA | GAA | GCA | AAG | GAG | AAC | AGA | AAC | CAC | CAG | CCA | CCT | CAA | CCC | AAG | GCC |
|-----|-----|-----|-----|-----|-----|-----|-----|-----|-----|-----|-----|-----|-----|-----|-----|
| Ile | Glu | Ala | Lys | Glu | Asn | Arg | Asn | His | Gln | Pro | Pro | Gln | Pro | Lys | Ala |

| TTG | GGC | AAT | CAG | CAG | CCT | TCG | TGG | GAT | TCA | GAG | GAT | AGC | AGC | AAC | TTC |
|-----|-----|-----|-----|-----|-----|-----|-----|-----|-----|-----|-----|-----|-----|-----|-----|
| Leu | Gly | Asn | Gln | Gln | Pro | Ser | Trp | Asp | Ser | Glu | Asp | Ser | Ser | Asn | Phe |

| AAA | GAT | GTA | GGT | TCA | AAA | GGC | AAA | GTT | GGT | AGA | CTC | TCT | GCT | CCA | GGT |
|-----|-----|-----|-----|-----|-----|-----|-----|-----|-----|-----|-----|-----|-----|-----|-----|
| Lys | Asp | Val | Gly | Ser | Lys | Gly | Lys | Val | Gly | Arg | Leu | Ser | Ala | Pro | Gly |

| TCT | CAA | CGT | GAA | GGA | AGG | AAC | CCC | CAG | CTG | AAC | CAG | CAA | TGA |
|-----|-----|-----|-----|-----|-----|-----|-----|-----|-----|-----|-----|-----|-----|
| Ser | Gln | Arg | Glu | Gly | Arg | Asn | Pro | Gln | Leu | Asn | Gln | Gln | |

TAATGATGGC CTCTCTCAAA AGAGAAAAAC AAAACCCCTA AGAGACTGAG TTCTGCAAGC

ATCAGTTCTA CGGATCATCA ACAAGATTTC CTTGTGCAAA ATATTTGACT ATTCTGTATC

TTTCATCCTT GACTAAATTC GTGATTTTCA AGCAGCATCT TCTGGTTTAA ACTTGTTTGC

TGTGAACAAT TGTCGAAAAG AGTCTTCCAA TTAATGCTTT TTTATATCTA GGCTACCTGT

TGGTTAGATT CAAGGCCCCC GAGCTGTTAC CATTCACAAT AAAAGCTTAA ACAC (SEQ ID NO: 14)

FIG. 4

SEQUENCE LISTING ( 1 ) GENERAL INFORMATION:

( i i i ) NUMBER OF SEQUENCES: 19

( 2 ) INFORMATION FOR SEQ ID NO: 1:

( i ) SEQUENCE CHARACTERISTICS:
        ( A ) LENGTH: 27
        ( B ) TYPE: amino acid
        ( C ) STRANDEDNESS:
        ( D ) TOPOLOGY: linear ( x i ) SEQUENCE DESCRIPTION: SEQ ID NO: 1:

Met Leu Val Lys Arg Ala Arg Cys Leu Leu Ser Cys His Ala Ser Gly
1               5                   10                  15

Gln Gly Cys Leu Gly Ile Pro Gly His Leu Met
            20                  25

( 2 ) INFORMATION FOR SEQ ID NO: 2:

( i ) SEQUENCE CHARACTERISTICS:
        ( A ) LENGTH: 22
        ( B ) TYPE: amino acid
        ( C ) STRANDEDNESS:
        ( D ) TOPOLOGY: linear ( x i ) SEQUENCE DESCRIPTION: SEQ ID NO: 2:

Ala Arg Cys Leu Leu Ser Cys His Ala Ser Gly Gln Gly Cys Leu Gly
1               5                   10                  15

Ile Pro Gly His Leu Met
            20

( 2 ) INFORMATION FOR SEQ ID NO: 3:

( i ) SEQUENCE CHARACTERISTICS:
        ( A ) LENGTH: 11
        ( B ) TYPE: amino acid
        ( C ) STRANDEDNESS:
        ( D ) TOPOLOGY: linear ( x i ) SEQUENCE DESCRIPTION: SEQ ID NO: 3:

Gln Gly Cys Leu Gly Ile Pro Gly His Leu Met
1               5                   10

( 2 ) INFORMATION FOR SEQ ID NO: 4:

( i ) SEQUENCE CHARACTERISTICS:
        ( A ) LENGTH: 27
        ( B ) TYPE: amino acid
        ( C ) STRANDEDNESS:
        ( D ) TOPOLOGY: linear ( x i ) SEQUENCE DESCRIPTION: SEQ ID NO: 4:

Met Leu Val Lys Arg Ala Ser Tyr Leu Leu Ser Cys His Thr Ser Gly
1               5                   10                  15

Gln Ser Cys Leu Gly Ile Pro Gly His Leu Met
            20                  25

( 2 ) INFORMATION FOR SEQ ID NO: 5:

( i ) SEQUENCE CHARACTERISTICS:
        ( A ) LENGTH: 22
        ( B ) TYPE: amino acid
        ( C ) STRANDEDNESS:
        ( D ) TOPOLOGY: linear ( x i ) SEQUENCE DESCRIPTION: SEQ ID NO: 5:

```
Ala Ser Tyr Leu Leu Ser Cys His Thr Ser Gly Gln Ser Cys Leu Gly
 1               5                  10                  15
Ile Pro Gly His Leu Met
            20
```

( 2 ) INFORMATION FOR SEQ ID NO: 6:

( i ) SEQUENCE CHARACTERISTICS:
        ( A ) LENGTH: 11
        ( B ) TYPE: amino acid
        ( C ) STRANDEDNESS:
        ( D ) TOPOLOGY: linear ( x i ) SEQUENCE DESCRIPTION: SEQ ID NO: 6:

```
Gln Ser Cys Leu Gly Ile Pro Gly His Leu Met
 1               5                  10
```

( 2 ) INFORMATION FOR SEQ ID NO: 7:

( i ) SEQUENCE CHARACTERISTICS:
        ( A ) LENGTH: 84
        ( B ) TYPE: nucleic acid
        ( C ) STRANDEDNESS: single
        ( D ) TOPOLOGY: linear ( x i ) SEQUENCE DESCRIPTION: SEQ ID NO: 7:

```
ATGCTTGTGA AAAGGGCCAG GTGTCTTCTG TCTTGCCATG CAAGTGGGCA GGGCTGCTTG    60
GGAATACCAG GGCACTTAAT GGGG    84
```

( 2 ) INFORMATION FOR SEQ ID NO: 8:

( i ) SEQUENCE CHARACTERISTICS:
        ( A ) LENGTH: 69
        ( B ) TYPE: nucleic acid
        ( C ) STRANDEDNESS: single
        ( D ) TOPOLOGY: linear ( x i ) SEQUENCE DESCRIPTION: SEQ ID NO: 8:

```
GCCAGGTGTC TTCTGTCTTG CCATGCAAGT GGGCAGGGCT GCTTGGGAAT ACCAGGGCAC    60
TTAATGGGG                                                            69
```

( 2 ) INFORMATION FOR SEQ ID NO: 9:

( i ) SEQUENCE CHARACTERISTICS:
        ( A ) LENGTH: 36
        ( B ) TYPE: nucleic acid
        ( C ) STRANDEDNESS: single
        ( D ) TOPOLOGY: linear ( x i ) SEQUENCE DESCRIPTION: SEQ ID NO: 9:

```
CAGGGCTGCT TGGGAATACC AGGCACTTA ATGGGG    36
```

( 2 ) INFORMATION FOR SEQ ID NO: 10:

( i ) SEQUENCE CHARACTERISTICS:
        ( A ) LENGTH: 84
        ( B ) TYPE: nucleic acid
        ( C ) STRANDEDNESS: single
        ( D ) TOPOLOGY: linear ( x i ) SEQUENCE DESCRIPTION: SEQ ID NO: 10:

| | | | | |
|---|---|---|---|---|
| ATGCTTGTGA | AAAGGGCCAG | CTATCTTCTG | TCTTGCCATA | CAAGTGGGCA | GAGCTGCCTG | 60 |
| GGAATACCAG | GGCACTTAAT | GGGG | | | | 84 |

( 2 ) INFORMATION FOR SEQ ID NO: 11:

( i ) SEQUENCE CHARACTERISTICS:
        ( A ) LENGTH: 69
        ( B ) TYPE: nucleic acid
        ( C ) STRANDEDNESS: single
        ( D ) TOPOLOGY: linear ( x i ) SEQUENCE DESCRIPTION: SEQ ID NO: 11:

| | | | | | | |
|---|---|---|---|---|---|---|
| GCCAGCTATC | TTCTGTCTTG | CCATACAAGT | GGGCAGAGCT | GCCTGGGAAT | ACCAGGGCAC | 60 |
| TTAATGGGG | | | | | | 69 |

( 2 ) INFORMATION FOR SEQ ID NO: 12:

( i ) SEQUENCE CHARACTERISTICS:
        ( A ) LENGTH: 36
        ( B ) TYPE: nucleic acid
        ( C ) STRANDEDNESS: single
        ( D ) TOPOLOGY: linear ( x i ) SEQUENCE DESCRIPTION: SEQ ID NO: 12:

CAGAGCTGCC TGGGAATACC AGGGCACTTA ATGGGG    36

( 2 ) INFORMATION FOR SEQ ID NO: 13:

( i ) SEQUENCE CHARACTERISTICS:
        ( A ) LENGTH: 645
        ( B ) TYPE: nucleic acid
        ( C ) STRANDEDNESS: single
        ( D ) TOPOLOGY: linear ( x i ) SEQUENCE DESCRIPTION: SEQ ID NO: 13:

| | | | | | |
|---|---|---|---|---|---|
| GGCAACTCTA | GAGGGGTGTG | TATGTGGCAG | TTCAGGGACA | GTTTGAGCTT | TCGGGTAGAG | 60 |
| GCAGCCTAGG | GAAACCGGCA | TAAAGCAGTT | TCTTTCTCTA | TTCCATGGAA | GCTGC | 115 |

```
ATG  CTT  GTG  AAA  AGG  GCC  AGG  TGT  CTT  CTG  TCT  TGC  CAT  GCA  AGT  GGG    163
Met  Leu  Val  Lys  Arg  Ala  Arg  Cys  Leu  Leu  Ser  Cys  His  Ala  Ser  Gly
 1                    5                    10                   15

CAG  GGC  TGC  TTG  GGA  ATA  CCA  GGG  CAC  TTA  ATG  GGG  AAA  AAG  AGC  ACA    211
Gln  Gly  Cys  Leu  Gly  Ile  Pro  Gly  His  Leu  Met  Gly  Lys  Lys  Ser  Thr
                20                   25                   30

GGG  GAG  TCT  TCT  GTT  TCT  GAG  AGA  GGG  AGC  CTA  AAG  CAG  CAG  CTG  AGA    259
Gly  Glu  Ser  Ser  Val  Ser  Glu  Arg  Gly  Ser  Leu  Lys  Gln  Gln  Leu  Arg
           35                   40                   45

GAG  TAC  ATC  AGG  TGG  GAA  GAA  GCT  GCA  AGC  AAT  TTG  CTG  GGT  CTC  ATA    307
Glu  Tyr  Ile  Arg  Trp  Glu  Glu  Ala  Ala  Ser  Asn  Leu  Leu  Gly  Leu  Ile
      50                   55                   60

GAA  GCA  AAG  GAG  AAC  AGA  AAC  CAC  CAG  CCA  CCT  CAA  CCC  AAG  GCC  CTG    355
Glu  Ala  Lys  Glu  Asn  Arg  Asn  His  Gln  Pro  Pro  Gln  Pro  Lys  Ala  Leu
 65                   70                   75                   80

GGC  AAT  CAG  CAG  CCT  TCG  TGG  GAT  TCA  GAG  GAT  AGC  AGC  AAC  TTC  AAA    403
Gly  Asn  Gln  Gln  Pro  Ser  Trp  Asp  Ser  Glu  Asp  Ser  Ser  Asn  Phe  Lys
                85                   90                   95

GAT  GTA  GGT  TCA  AAA  GGC  AAA  GTT  GGT  AGA  CTC  TCT  GCT  CCA  GGT  TCT    451
Asp  Val  Gly  Ser  Lys  Gly  Lys  Val  Gly  Arg  Leu  Ser  Ala  Pro  Gly  Ser
           100                  105                  110

CAA  CGT  GAA  GGA  AGG  AAC  CCC  CCA  GCT  GAA  CCA  GCA  ATG  ACA  ATG  ATG    499
Gln  Arg  Glu  Gly  Arg  Asn  Pro  Pro  Ala  Glu  Pro  Ala  Met  Thr  Met  Ala
      115                  120                  125
```

```
GCC TCT CTC AAA GGA GAA AAA CAA AAC CCG TAA GAGACTGCGT TCTGCAAGCA    552
Ala Ser Leu Lys Gly Glu Lys Gln Asn Pro
        130                 135

TCAGTTCTAC GGATCATCAA CAAGATTTCC TTGTGCAAAA TATTTGACTA TTCTTGTATC    612

TTTCATCCTT GACTAAATTC GTGATTTTCA AGC                                 645
```

( 2 ) INFORMATION FOR SEQ ID NO: 14:

( i ) SEQUENCE CHARACTERISTICS:
        ( A ) LENGTH: 787
        ( B ) TYPE: nucleic acid
        ( C ) STRANDEDNESS: single
        ( D ) TOPOLOGY: linear ( x i ) SEQUENCE DESCRIPTION: SEQ ID NO: 14:

```
AGCAACTCTA GAGGGGTGTG TATGTGGCAG TTTAGGGACA GTTGAGCTT TCAGGTAGAG      60

GCAGCCTAGG GAAACTGGCA TAAAGCAGTT TCTTTCTCTA TTCCATGGAA GTTGC         115

ATG CTT GTG AAA AGG GCC AGC TAT CTT CTG TCT TGC CAT ACA AGT GGG      163
Met Leu Val Lys Arg Ala Ser Tyr Leu Leu Ser Cys His Thr Ser Gly
 1               5                  10                  15

CAG AGC TGC CTG GGA ATA CCA GGG CAC TTA ATG GGG AAA AAG AGC ACA      211
Gln Ser Cys Leu Gly Ile Pro Gly His Leu Met Gly Lys Lys Ser Thr
             20                  25                  30

GGG GAG TCT TCT TCT GTT TCT GAG AGA GGG AGC CTG AAG CAG CAG CTG      259
Gly Glu Ser Ser Ser Val Ser Glu Arg Gly Ser Leu Lys Gln Gln Leu
         35                  40                  45

AGA GAG TAC ATC AGG TGG GAA GAA GCT GCA AGG AAT TTG CTG GGT CTC      307
Arg Glu Tyr Ile Arg Trp Glu Glu Ala Ala Arg Asn Leu Leu Gly Leu
     50                  55                  60

ATA GAA GCA AAG GAG AAC AGA AAC CAC CAG CCA CCT CAA CCC AAG GCC      355
Ile Glu Ala Lys Glu Asn Arg Asn His Gln Pro Pro Gln Pro Lys Ala
 65                  70                  75                  80

TTG GGC AAT CAG CAG CCT TCG TGG GAT TCA GAG GAT AGC AGC AAC TTC      403
Leu Gly Asn Gln Gln Pro Ser Trp Asp Ser Glu Asp Ser Ser Asn Phe
                 85                  90                  95

AAA GAT GTA GGT TCA AAA GGC AAA GTT GGT AGA CTC TCT GCT CCA GGT      451
Lys Asp Val Gly Ser Lys Gly Lys Val Gly Arg Leu Ser Ala Pro Gly
             100                 105                 110

TCT CAA CGT GAA GGA AGG AAC CCC CAG CTG AAC CAG CAA TGA              493
Ser Gln Arg Glu Gly Arg Asn Pro Gln Leu Asn Gln Gln
         115                 120                 125

TAATGATGGC CTCTCTCAAA AGAGAAAAAC AAAACCCCTA AGAGACTGAG TTCTGCAAGC    553

ATCAGTTCTA CGGATCATCA ACAAGATTTC CTTGTGCAAA ATATTTGACT ATTCTGTATC    613

TTTCATCCTT GACTAAATTC GTGATTTTCA AGCAGCATCT TCTGGTTTAA ACTTGTTTGC    673

TGTGAACAAT TGTCGAAAAG AGTCTTCCAA TTAATGCTTT TTTATATCTA GGCTACCTGT    733

TGGTTAGATT CAAGGCCCCC GAGCTGTTAC CATTCACAAT AAAAGCTTAA ACAC          787
```

( 2 ) INFORMATION FOR SEQ ID NO: 15:

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: linear ( x i ) SEQUENCE DESCRIPTION: SEQ ID NO: 15:

```
GTAGACTCTC TGCTCCAG                          18
```

( 2 ) INFORMATION FOR SEQ ID NO: 16:

( i ) SEQUENCE CHARACTERISTICS:

(A) LENGTH: 18
(B) TYPE: nucleic acid
(C) STRANDEDNESS: single
(D) TOPOLOGY: linear ( x i ) SEQUENCE DESCRIPTION: SEQ ID NO: 16:

AAACCAGAAG ATGCTGCT          18

( 2 ) INFORMATION FOR SEQ ID NO: 17:

( i ) SEQUENCE CHARACTERISTICS:
(A) LENGTH: 21
(B) TYPE: nucleic acid
(C) STRANDEDNESS: single
(D) TOPOLOGY: linear ( x i ) SEQUENCE DESCRIPTION: SEQ ID NO: 17:

GTGTATGTGG CAGTTCAGGG A          21

( 2 ) INFORMATION FOR SEQ ID NO: 18:

( i ) SEQUENCE CHARACTERISTICS:
(A) LENGTH: 16
(B) TYPE: nucleic acid
(C) STRANDEDNESS: single
(D) TOPOLOGY: linear ( x i ) SEQUENCE DESCRIPTION: SEQ ID NO: 18:

ATGGCAAGAC AGAAGA          16

( 2 ) INFORMATION FOR SEQ ID NO: 19:

( i ) SEQUENCE CHARACTERISTICS:
(A) LENGTH: 17
(B) TYPE: nucleic acid
(C) STRANDEDNESS: single
(D) TOPOLOGY: linear ( x i ) SEQUENCE DESCRIPTION: SEQ ID NO: 19:

TGCATGCTTG TGAAAAG          17

DNA SEQUENCE WHICH ENCODES A PEPTIDE CAPABLE OF PROMOTING ACROSOME REACTION

STATEMENT AS TO FEDERALLY SPONSORED RESEARCH

This invention was made with support from the National Institute of Health (Grant No. R01-CA39237). Accordingly, the U.S. government has certain rights in the invention.

CROSS REFERENCE TO RELATED APPLICATIONS

This application is a continuation-in-part of U.S. patent application Ser. No. 07/919,731, filed Jul. 27, 1992 now abandoned.

FIELD OF THE INVENTION

The present invention relates generally to the manipulation of genetic materials, and, more particularly, to recombinant procedures making possible the identification of DNA sequences encoding peptides which possess a specific property and the encoded peptides.

BACKGROUND OF THE INVENTION

At present, the overall success rate for in vitro fertilization is approximately 20–25%. This figure includes multiple attempts (up to 3–4 times by some couples) to succeed. Thus, any process which can increase the efficiency of fertilization will have significant utility for in vitro fertilization procedures.

On the other hand, it is estimated that there are 1.5 to 2 million pregnancies that occur in the United States alone because of failures in contraception. Failure rates of vaginal contraceptives such as foam or jelly, either alone or in combination with condoms or diaphragm, range from 2–20% per year depending on conditions and the study cited. See Developing New Contraceptive: Obstacles and Opportunities, Washington D.C., National Academy Press (1990). Therefore, any minor improvement in the efficiency of contraceptives, thousands of accidental or unwanted pregnancies could be prevented per year.

Bombesin, a tetradecapeptide amide first isolated from the skin of the frog *Bombina bombina*, is a potent mitogen for mouse Swiss 3T3 fibroblast cells. It also stimulates secretion for guinea pig pancreatic acini. Bombesin-like peptides are produced and secreted by human small cell lung cancer cells ("SCLC") and exogenously added bombesin-like peptides can stimulate the growth of human SCLC cells in vitro. Two examples of bombesin-like peptides are gastrin releasing peptide ("GRP") and Neuromedin C.

GRP is a 27 amino acid peptide amide first isolated from the porcine gut. The C-terminal amino acid sequence of GRP is almost identical to that of bombesin. Neuromedin C is a decapeptide amide, the structure of which is identical to the last ten amino acids in the C-terminal region of GRP. Both GRP and Neuromedin C share amino acid sequence homology with bombesin and possess bombesin-like properties. Other bombesin-like peptides include litorin and Neuromedin B.

GRP is encoded by a gene located on the 18th chromosome. Naylor et al. Somat. Cell Mol. Genet. 13:87 (1987). GRP is encoded by 3 exons with exon 1 encoding the first 23 amino acids of GRP and exon 2 the latter 4 amino acids. Spindel et al. Mol. Endocrinol. 1:224 (1987). The GRP prohormone includes a signal peptide, the sequence of GRP, a dibasic amino acid cleavage site, and a long C-terminal peptide following the cleavage site. Bioactive GRP is processed from the prohormone basically in 3 steps; first by removal of the signal peptide, second by cleavage of the C-terminal peptide at the dibasic site, and third by amidation of GRP. GRP itself may then be further cleaved to give the C-terminal decapeptide of GRP (GRP-10) which has similar bioactivity as does GRP.

For fertilization to occur, sperm must undergo an exocytotic process called the acrosome reaction which enables sperm to penetrate the external layers of the ova. It has not been reported hitherto that bombesin or bombesin-like peptides are capable of increasing or decreasing the efficiency of fertilization of eggs by sperm by promoting acrosome reaction.

SUMMARY OF THE INVENTION

The present invention features a pure DNA encoding a peptide which is capable of promoting acrosome reaction and identified herein as SEQ ID NO: 1, SEQ ID NO: 2, SEQ ID NO: 3, SEQ ID NO: 4, SEQ ID NO: 5, or SEQ ID NO: 6. Preferably, the DNA of this invention consists essentially of a nucleotide sequence identified herein as SEQ ID NO: 7, SEQ ID NO: 8, SEQ ID NO: 9, SEQ ID NO: 10, SEQ ID NO: 11, or SEQ ID NO: 12.

Also within this invention is a vector or a cell containing one of the above-described DNA sequences. Preferably, in a cell which contains the DNA of the invention, the DNA is introduced into the cell in a manner allowing the cell to express the peptide.

The present invention further features a pure peptide identified herein as SEQ ID NO: 1, SEQ ID NO: 2, SEQ ID NO: 3, SEQ ID NO: 4, SEQ ID NO: 5, or SEQ ID NO: 6.

A pharmaceutical composition which includes one of the above-described peptides and a pharmaceutically acceptable carrier is an additional feature of the present invention.

A still another feature of the present invention is a method of promoting fertilization. The method includes the step of contacting sperm either at the time of sperm capacitation or at the time of egg fertilization with an effective amount of one of the above-described peptides. Note that for fertilization to occur, sperm must undergo an exocytotic process called the acrosome reaction which enables sperm to penetrate the external layers of the ova. For the acrosome reaction to occur, sperm must undergo the process of capacitation. The operational definition of capacitation is simply the ability of sperm to undergo the acrosome reaction.

It is a further feature of the present invention to prepare one of the above-described peptides by a DNA recombinant method which includes the steps of (i) introducing a DNA encoding the peptide into cells in a manner allowing the cells to express the peptide; (ii) culturing the cells in a medium; and (iii) recovering the expressed peptide.

What is meant by "pure DNA" herein is DNA that is not immediately contiguous with both of the coding sequences with which it is immediately contiguous (i.e., one at the 5′ end and one at the 3′ end) in the naturally-occurring genome of the organism from which the DNA of the invention is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA or a genomic DNA fragment produced by polymerase chain reaction or restriction endonuclease treatment) independent of other DNA sequences. It also includes a recombinant DNA which is part of a hybrid gene encoding additional polypeptide sequence.

A pure peptide, on the other hand, is a peptide which is free or substantially free of the components with which it naturally occurs.

Other features and advantages of the invention will be apparent from the following description and from the claims.

BRIEF DESCRIPTION OF THE DRAWINGS

The drawings are first briefly described.

FIG. 1 is a sequence and translation of a rhesus monkey cDNA encoding peptides capable of promoting acrosome reaction.

FIG. 4 is a sequence and translation of a human cDNA encoding peptides capable of promoting acrosome reaction.

DESCRIPTION OF THE PREFERRED EMBODIMENTS

Figure 2:
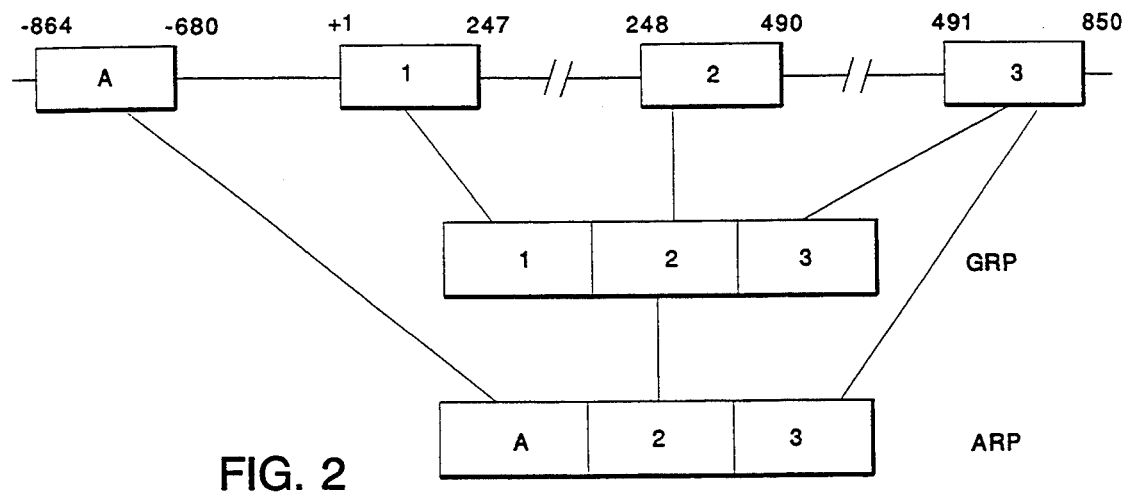
FIG. 2 is a schematic representation of the mechanism by which a mRNA encoding acrosome reaction-promoting peptides is produced in human testes.

High levels of mRNA that hybridizes to the human GRP cDNA were found to be present in monkey testes. Northern blot analysis clearly shows that GRP mRNA present in monkey testes in higher concentrations than in non-neoplastic tissue such as lung. In addition, in situ hybridization has clearly localized the GRP mRNA to developing sperm.

Sequence analysis of partial cDNA clones (which lacked the 5'-end of the mRNA and the coding region for the bombesin-like peptide) derived from a monkey testes cDNA library shows that the hybridizing monkey mRNA is clearly related to human GRP. Furthermore, hybridization study suggests that the 5'-end of this mRNA may be different from that of GRP and could thus encode a new bombesin-like peptide (i.e., other than GRP). Described below is the procedures used by us to successfully clone a mRNA from monkey testes which encodes such a new peptide.

A cDNA probe for exon 3 of monkey GRP was first generated by the following method. (The structure of the monkey GRP gene, including designation of exons, is provided below.)

Two 17-base oligonucleotides corresponding to sequences in exon 3 of monkey GRP, i.e., GTAGACTCTCTGCTCCAG (SEQ ID NO: 15) and AAACCAGAAGATGCTGCT (SEQ ID NO: 16), were used to amplify the corresponding DNA sequence from rhesus monkey genomic DNA by the polymerase chain reaction ("PCR"). The sequence of the 5'-terminal segment of the probe is shown in FIG. 1 (in dashed box). The monkey genomic DNA was purchased from a commercial source (Clonetech, Palo Alto, Calif.). PCR conditions were 35 cycles of 1 min. at 92° C., 2 min. at 55° C., 2 min. at 72° C.

The resulting band was subcloned into the vector BluescriptII (Stratagene, La Jolla, Calif.) following standard procedures as described by Ausubel et al. Current Protocols in Molecular Biology, John Wiley & Sons, New York (1987), which is hereby incorporated by reference. The sequence of the subcloned DNA as monkey GRP exon 3 was confirmed by DNA sequence analysis using double-stranded template as described in Chen, E. Y. et al., DNA 4:165 (1985)(which is hereby incorporated by reference) and flanking primers in the vector. The subcloned DNA was subsequently used to prepare a probe to screen a monkey testes cDNA library which was constructed as follows.

Rhesus monkey testes were collected from sacrificed monkeys. Total RNA was prepared using guanidine thiocyanate and CsCl ultracentrifugation as described in Chirgwin J. M. et al. Biochemistry 18:5294 (1979), which is hereby incorporated by reference. Poly(A) RNA was prepared using oligo (dT) cellulose. See Ausubel et al. id. A cDNA library was prepared in the vector λZapII using reagents and protocols supplied by Stratagene (UniZap Cloning Kit) as described previously. Nagalla, S. R. et al. J. Biol. Chem. 267:6916 (1992), which is hereby incorporated by reference.

The library, which contained greater than $2 \times 10^6$ independent clones with an average insert size of 1–1.5 kb, was plated, transferred to nitrocellulose, UV cross-linked, and screened with the monkey GRP exon 3 probe. For library screening, the probe was prepared as a $^{32}$P-labeled antisense cRNA probe using the T7RNA polymerase promoter present in the vector. Hybridization conditions were 50% formamide/5× SSC/5× Denhardt's/50 mM sodium phosphate, pH 7.0/2.5% SDS/200 μg/ml sonicated denatured salmon sperm/200 μg yeast RNA at 42° for 18 hr. Blots were washed for two 15 min. intervals in 2× SSC/0.1% SDS at 50°. Approximately 45 hybridizing clones were identified. Some of the hybridizing clones were plaque purified and the cDNA inserts were excised into the vector bluescript using helper phage (following Stratagene protocol). Plasmid DNA was prepared according to standard methods [Ausubel et al. id.] and sequenced as described above.

The nucleotide sequence of the monkey cDNA thus obtained, as well as the deduced amino acid sequence, is shown in FIG. 1. Because mRNA corresponding to the FIG. 1 cDNA has been identified in spermatocytes and the new bombesin-like peptides encoded by it play a role in the acrosome reaction, the new peptides are designated herein acrosome-related peptides ("ARP's").

In FIG. 1, the sequence of the probe used to identify ARP's is indicated by a dashed box, and the sites of intron-exon boundaries based on homology with the human GRP gene (Spindel et al., id.) are indicated by solid triangles. The probe used to identify the ARP cDNA lies in exon 3. The C-terminal extension peptide of the ARP prohormone is encoded on exons 2 and 3, all but the C-terminal 4 amino acids of ARP's are encoded in exon A, and the C-terminal 4 amino acids of ARP's are encoded in exon 2. The above designation of exons in monkey GRP gene is identical to that for human GRP gene (see FIG. 2 and its accompanying text below).

In FIG. 1, the sequence encoding ARP's and the glycine for the carboxy-terminal amide are underlined.

The C-terminal glycine serves as the amide donor for the C-terminal methionyl-amide residue of an ARP's. Bradbury et al. Nature 298:686 (1982). The two dibasic cleavage sites, Lys-Arg and Lys-Lys, are overlined. Douglass et al. Annu. Rev. Biochem, 53:665 (1984).

ARP's play an important role in regulating the efficiency of fertilization of eggs by sperm. Hence, the peptides themselves and their agonists can be used to promote fertilization. On the other hand, their antagonists have contraceptive utility.

Based on the amino acid sequence of FIG. 1 and known active bombesin-like peptides (e.g., GRP), biologically active ARP's include the following (respective numbers of amino acid residues are given):

(1) Monkey ARP-27:
H-Met-Leu-Val-Lys-Arg-Ala-Arg-Cys-Leu-Leu-Ser-Cys-His -Ala-Ser-Gly-Gln-Gly-Cys-Leu-Gly-Ile-Pro-Gly-His-Leu -Met.NH$_2$ (SEQ ID NO: 1);

(2) Monkey ARP-22:
H-Ala-Arg-Cys-Leu-Leu-Ser-Cys-His-Ala-Ser-Gly-Gln-Gly   -Cys-Leu-Gly-Ile-Pro-Gly-His-Leu-Met.NH$_2$ (SEQ ID NO: 2); and (3) Monkey ARP-11:
H-Gln-Gly-Cys-Leu-Gly-Ile-Pro-Gly-His-Leu-Met.NH$_2$ (SEQ ID NO: 3).

Except for Pro, all three-letter abbreviations of amino acids in this disclosure stand for a residue with the structure of —NH—CH(R)—CO—, wherein R is a side chain. The symbol Pro stands for the structure of

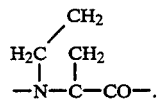

Monkey ARP-27, monkey ARP-22 and monkey ARP-11 are encoded by the following segments in the cDNA sequences in FIG. 1, respectively:

ATGCTTGTGAAAAGGG-CCAGGTGTCTTCTGTCTTGCCATG-CAAGTGGGCAG    GGCTGCTTGGGAATAC-CAGGGCACTTAATGGGG (SEQ ID NO: 7);

GCCAGGTGTCTTCTGTCTTGCCATG-CAAGTGGGCAGGGCTGCTTGGGAATA CCAGGGCACTTAATGGGG (SEQ ID NO: 8); and

CAGGGCTGCTTGGGAATACCAGGGCACT-TAATGGGG (SEQ ID NO: 9);

The human GRP gene was cloned as described in Spindel et al. Mol. Endocrinolo 1:224 (1987), which is hereby incorporated by reference. Sequence of the 5'-flanking region up to base −534 was obtained as described in that reference. Additional sequence was obtained by subcloning a XmaI-XmaI fragment corresponding to bases −1705 to −24 of the 5'-flanking region of the human GRP gene from the same genomic clone used in Spindel et al., id. This fragment was subcloned into the vector PGEM3 and sequenced as described by Chen et al., id. using flanking primers in the vector and internal primers from derived sequence.]

The nucleotide sequence of all exons and some introns of the human GRP gene can be found in FIG. 2 of Spindel id. and FIG. 4 herein below. As will be discussed immediately below, DNA sequence consisting of the first 185 nucleotides in FIG. 4 is part of a newly found exon and corresponds to sequence −864 to −680 in FIG. 2, Spindel. et al. id., which is hereby incorporated in its entirety. Furthermore, the numbering system in FIG. 2 thereof is adopted for the human GRP gene throughout this disclosure.

Comparison of the sequence of the monkey ARP cDNA with the sequence of the human GRP gene clearly indicates how ARP's arise from the human GRP gene and also explicitly predicts the amino acid sequences of human ARP's. More specifically, the sequence of the monkey ARP cDNA consisting of the first 185 nucleotides (FIG. 1) is nearly identical to bases −864 to −680 of the human GRP gene relative to the transcriptional start site as described by Spindel et al. id. The remainder of the cDNA sequence of monkey ARP's (from base 186 to the 3' end) is nearly identical to the segment covering base 248 to base 709 of the human GRP gene sequence. Base 248 corresponds to the beginning of exon 2 of the human GRP gene. Thus, the ARP mRNA arises by initiation of transcription of a hitherto unknown exon (named "exon A" herein) of the GRP gene at approximately 864 base upstream from the transcriptional start described in Spindel et al., id., followed by splicing of this new exon into the previously described exons 2 and 3 of the GRP gene. See FIG. 2, which shows both a schematic representation of the structure of the human GRP gene (top) and mechanisms by which the GRP mRNA and the ARP mRNA are produced in different tissues.

More specifically, while a standard transcriptional initiation site is used and exons 1, 2 and 3 of the GRP gene in most tissues are spliced together to produce GRP (see Spindel et al., id.), an upstream promoter is used to initiate transcription at approximately base −864 relative to the standard site of initiation in testes to produce a mRNA with an additional exon, exon A. Exon A is then spliced to exons 2 and 3, thereby giving the processed mRNA which encodes ARP's in testes.

Note that determination of intron between exon A and exon 1 was based on decreased sequence homology between the monkey cDNA and human gene sequences, and the presence of an intron donor site consensus sequence (GTGGG) in the human GRP promoter sequence.

Figure 3:
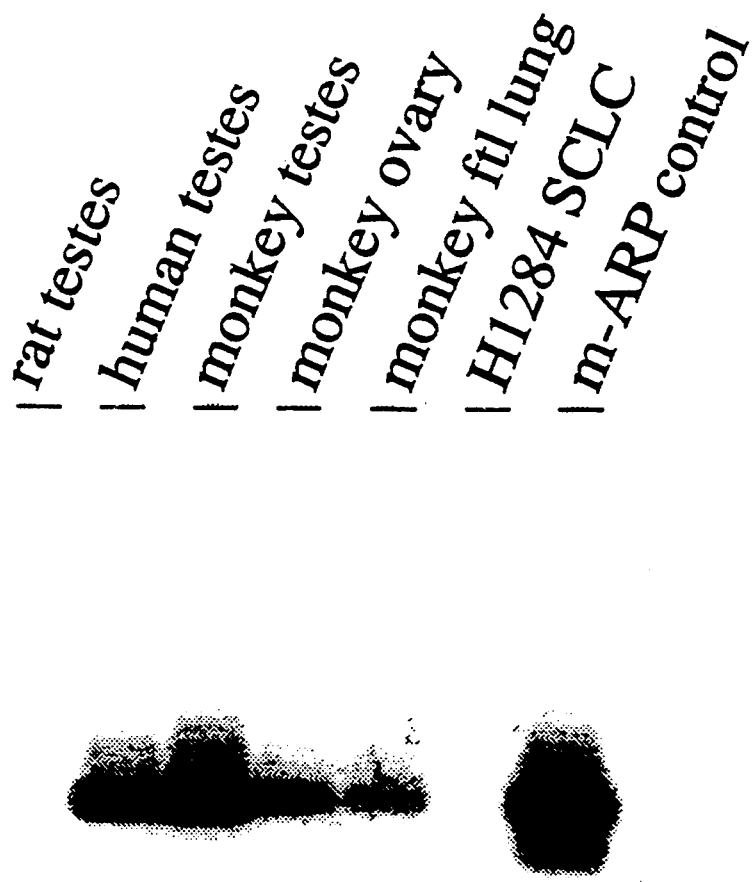
FIG. 3 is a graph showing distribution of mRNA encoding acrosome reaction-promoting peptides by polymerase chain reaction.

As shown in FIG. 3, PCR analysis confirms the existence of the ARP mRNA in human testes. More specifically, RNA from the tissues shown above were reverse transcribed and then amplified by the PCR using a pair of primers that spanned exon A of the GRP gene, i.e., GTGTATGTGGCAGTTCAGGGA (SEQ ID NO: 17) and ATGGCAAGACAGAAGA (SEQ ID NO: 18). Amplified DNA was separated by gel electrophoresis, transferred to nylon membranes and detected by hybridization to a probe corresponding to a sequence internal to the two primers used for amplification (i.e., TGCATGCTTGTGAAAAG (SEQ ID NO: 19).

The intensity of hybridization in human testes is similar to that observed in monkey testes.. PCR analysis also indicates that ARP mRNA is expressed in cervix, oviduct, uterus, ovary and fetal lung. Thus, the ARP mRNA has a wide distribution in human tissues and its encoded peptides have a variety of physiologic and pathologic roles. These include effects on efficiency of fertilization of eggs by sperm as well as effects on the growth of neoplastic tissues and the regulation of gastrointestinal functions.

The sequence and translation of the human ARP cDNA which is determined based on the close homology between the monkey and human DNA sequences are shown in FIG. 4. The sequence encoding the bioactive peptides and the glycine for the carboxy-terminal amide are underlined. The two dibasic cleavage sites (Lys-Arg and Lys-Lys), on the other hand, are overlined.

Thus, human ARP's have the following sequences which are highly homologous to their simian counterparts:

(1) Human ARP-27:
H-Met-Leu-Val-Lys-Arg-Ala-Ser-Tyr-Leu-Leu-Ser-Cys-His -Thr-Ser-Gly-Gln-Ser-Cys-Leu-Gly-Ile-Pro-Gly-His-Leu -Met.NH$_2$ (SEQ ID NO: 4);

(2) Human ARP-22:
H-Ala-Ser-Tyr-Leu-Leu-Ser-Cys-His-Thr-Ser-Gly-Gln-Ser -Cys-Leu-Gly-Ile-Pro-Gly-His-Leu-Met.NH$_2$ (SEQ ID NO: 5); and (3) Human ARP-11:
H-Gln-Ser-Cys-Leu-Gly-Ile-Pro-Gly-His-Leu-Met.NH$_2$ (SEQ ID NO: 6).

Human ARP-27, human ARP-22 and human ARP-11 are encoded by the following segments in the cDNA sequences in FIG. 4, respectively:

ATGCTTGTGAAAAGGGCCAGC-TATCTTCTGTCTTGCCATACAAGTGGGCAG AGCTGCCTGGGAATACCAGGGCACT-TAATGGGG (SEQ ID NO: 10);

GCCAGCTATCTTCTGTCTTG-CCATACAAGTGGGCAGAGCTGCCTG-GGAATA CCAGGGCACTTAATGGGG (SEQ ID NO: 11); and

CAGAGCTGCCTGGGAATACCAGGGCACT-TAATGGGG
(SEQ ID NO: 12);

The presence of the ARP mRNA in both human and monkey testes suggested that ARP's, a newly discovered class of bombesin-like peptides, played a role in fertilization. Thus, it was proposed that bombesin, ARP's and other bombesin-like peptides had effects on the spontaneous acrosome reaction, which is necessary for sperm to fertilize the egg. Results from the following experiments confirmed that proposition.

For monkeys, sperm was collected, washed twice in balanced salts, resuspended in lactate/bicarbonate and dibutyryl cAMP, and then incubated for 60 minutes. These are the conditions which have been demonstrated to capacitate sperm for monkey in vitro fertilization. See Wolf, D. P. et al. Mol. Reprod. Dev. 27:261–280 (1990); Lanzendorf, S. E. et al. Mol. Reprod. Dev. 25:61–66 (1990); and Wolf D. P. et al. Biol. Reprod. 41:335–346 (1989). All of these three publications are hereby incorporated by reference.

To measure the effects of bombesin on the acrosome reaction, capacitation was conducted in the presence or absence of bombesin. After incubation, samples of sperm were removed to determine the percentage of sperm which had undergone the acrosome reaction as measured with an acrosome specific monoclonal antibody and FITC fluorescence [see Wolf, D. P. Am. J. Reprod. Immunol. 20:106–113 (1989), which is hereby incorporated by reference].

For human sperm, capacitation was achieved by overnight incubation of sperm in balanced salt and 0.3% bovine serum albumin, after which bombesin was added to induce the acrosome reaction.

Figure 5:
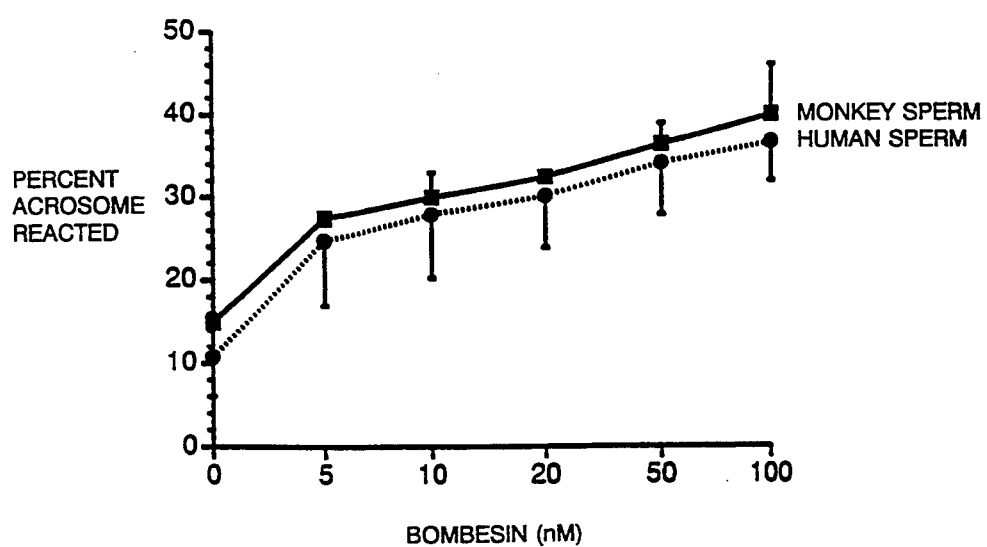
FIG. 5 is a graph showing effect of bombesin on induction of acrosome reaction.

As shown in FIG. 5, at a concentration as low as 5 nM, bombesin caused a 2-fold increase in the acrosome reaction in both monkey and human sperm.

Insertion of an ARP-encoding sequence into a vector and introduction of the recombinant vector into a host cell are desirable. For example, an ARP can be produced by such a host cell. Such techniques are well known to a person of ordinary skill in the art and in any event can be found in the literature, e.g., Sambrook, et al. Molecular Cloning, A Laboratory Manual, 2nd Ed. Cold Spring Harbor Laboratory Press, New York (1989), hereby incorporated by reference.

An ARP can also be used in a pharmaceutical composition. In a method of using an ARP to promote fertilization in both medical and veterinary applications, the effective amount of the ARP to be used varies depending upon the manner of administration and the condition of the subject to be treated, and ultimately will be decided by the attending physician or veterinarian.

OTHER EMBODIMENTS

The invention includes any peptide which is substantially homologous (i.e., 60% or greater) to human and rhesus monkey ARP's identified above as SEQ ID NO: 1, SEQ ID NO: 2, SEQ ID NO: 3, SEQ ID NO: 4, SEQ ID NO: 5, and SEQ ID NO: 6, as well as any naturally occurring peptide in other species which corresponds to one of the above-identified ARP's.

Homologous refers to the sequence similarity between two peptides. When a position in both of the two compared sequences is occupied by the same amino acid monomeric subunit. The homology between two sequences is a function of the number of matching or homologous positions shared by the two sequences. For example, 6 of 10 of the positions in two sequences are matched or homologous then the two sequences are 60% homologous.

Other ARP's which are also included in this invention are allelic variations, natural mutants, induced mutants, peptides encoded by DNA that hybridizes under high or low stringency conditions (see below) to SEQ ID NO: 7, SEQ ID NO: 8, SEQ ID NO: 9, SEQ ID NO: 10, SEQ ID NO: 11, or SEQ ID NO: 12, and peptides specifically bound by antisera to SEQ ID NO: 1, SEQ ID NO: 2, SEQ ID NO: 3, SEQ ID NO: 4, SEQ ID NO: 5, or SEQ ID NO: 6.

The invention also includes a pure DNA characterized as including a sequence which hybridizes under highly stringent conditions (e.g., as described in Sambrook et al., Molecular Cloning: A Laboratory Manual, Cold Spring Harbor Laboratory, Cold Spring Harbor, N.Y., 1989, hereby incorporated by reference) to a nucleic acid probe which includes at least a six-nucleotide segment (preferably at least 10 nucleotides) of SEQ ID NO: 7, SEQ ID NO: 8, SEQ ID NO: 9, SEQ ID NO: 10, SEQ ID NO: 11, or SEQ ID NO: 12. Alternatively, the DNA of the invention may be characterized as being capable of hybridizing under low-stringency conditions to a nucleic acid probe which includes the coding sequence of SEQ ID NO: 7, SEQ ID NO: 8, SEQ ID NO: 9, SEQ ID NO: 10, SEQ ID NO: 11, or SEQ ID NO: 12. An example of such low-stringency conditions is as follows: prehybridization in 50% formamide, 5× SSC, 25 mM potassium phosphate buffer (pH 7.4), 5× Denhardt's, and 50 µg/ml denatured salmon sperm DNA for 4–12 hours at 20° C.; hybridization for 12–24 hours at 20° C.; and washing in 5× SSC containing 0.1% SDS, at 20° C.

The invention also includes any biologically active analog of SEQ ID NO: 1, SEQ ID NO: 2, SEQ ID NO: 3, SEQ ID NO: 4, SEQ ID NO: 5, or SEQ ID NO: 6. By "biologically active" is meant possessing an acrosome reaction-promoting activity similar to or greater than that exhibited by bombesin as shown in FIG. 5. Most preferably, it possesses at least 75% of the activity of bombesin.

Analogs can differ from naturally occurring ARP's in amino acid sequence or can be modified in ways that do not involve sequence, or both. Alterations in primary sequence include genetic variants, both natural and induced. Also included are analogs that include residues other than naturally occurring L-amino acids.

The existence of the above-described active ARP's does not rule out the existence of other active bombesin-like peptides in the male and female reproductive tract, including GRP, NMB and potentially other not yet characterized bombesin-like peptides.

Other embodiments are also within the following claims.

What is claimed is:

1. A pure DNA encoding a peptide selected from the group consisting of SEQ ID NO: 1, SEQ ID NO: 2, SEQ ID NO: 3, SEQ ID NO: 4, SEQ ID NO: 5, and SEQ ID NO: 6.

2. The DNA of claim 1, wherein said peptide is SEQ ID NO: 2, SEQ ID NO: 3, SEQ ID NO: 5, or SEQ ID NO: 6.

3. The DNA of claim 2, wherein said peptide is SEQ ID NO: 3, or SEQ ID NO: 6.

4. The DNA of claim 1 is SEQ ID NO: 7, SEQ ID NO: 8, SEQ ID NO: 9, SEQ ID NO: 10, SEQ ID NO: 11, or SEQ ID NO: 12.

5. The DNA of claim 4 is SEQ ID NO: 8, SEQ ID NO: 9, SEQ ID NO: 11, or SEQ ID NO: 12.

6. The DNA of claim 5 is SEQ ID NO: 9, or SEQ ID NO: 12.

7. A recombinant vector containing the DNA of claim 1.

8. A recombinant vector containing the DNA of claim 4.

9. A host cell into which the vector of claim 7 was introduced.

10. A cell into which the vector of claim 8 was introduced.

11. The cell of claim 9, wherein said DNA is introduced into said cell in a manner allowing said cell to express said peptide.

12. The cell of claim 10, wherein said DNA is introduced into said cell in a manner allowing said cell to express said peptide.

13. A pure peptide selected from the group consisting of SEQ ID NO: 1, SEQ ID NO: 2, SEQ ID NO: 3, SEQ ID NO: 4, SEQ ID NO: 5, and SEQ ID NO: 6.

14. The peptide of claim 13 is SEQ ID NO: 2; SEQ ID NO: 3, SEQ ID NO: 5, or SEQ ID NO: 6.

15. The peptide of claim 2, wherein said peptide is SEQ ID NO: 3, or SEQ ID NO: 6.

16. A pharmaceutical composition comprising the peptide of claim 13 and a pharmaceutically acceptable carrier.

17. A pharmaceutical composition comprising the peptide of claim 14 and a pharmaceutically acceptable carrier.

18. A pharmaceutical composition comprising the peptide of claim 15 and a pharmaceutically acceptable carrier.

19. A method of promoting fertilization, said method comprising the step of contacting sperm either at the time of sperm capacitation or at the time of egg fertilization with an effective amount of the peptide of claim 13.

20. A method of promoting fertilization, said method comprising the step of contacting sperm either at the time of sperm capacitation or at the time of egg fertilization with an effective amount of the peptide of claim 14.

21. A method of promoting fertilization, said method comprising the step of contacting sperm either at the time of sperm capacitation or at the time of egg fertilization with an effective amount of the peptide of claim 15.

22. A method of preparing the peptide of claim 13, said method comprising the steps of
   introducing a DNA encoding said peptide into cells in a manner allowing said cells to express said peptide;
   culturing said cells in a medium; and
   recovering said expressed peptide.

23. A method of preparing the peptide of claim 14, said method comprising the steps of
   introducing a DNA encoding said peptide into cells in a manner allowing said cells to express said peptide;
   culturing said cells in a medium; and
   recovering said expressed peptide.

24. A method of preparing the peptide of claim 15, said method comprising the steps of
   introducing a DNA encoding said peptide into cells in a manner allowing said cells to express said peptide;
   culturing said cells in a medium; and
   recovering said expressed peptide.

* * * * *

UNITED STATES PATENT AND TRADEMARK OFFICE
CERTIFICATE OF CORRECTION

PATENT NO.   : 5,436,137

DATED        : July 25, 1995

INVENTOR(S)  : Eliot R. Spindel, Srinivasan Vijayaraghavan, Srinivasa R. Nagalla, and Kang Li It is certified that error appears in the above-identified patent and that said Letters Patent is hereby corrected as shown below:

On the title page, second column, under "PUBLICATIONS", correct the following:

"Gavessi" should be --Gnessi--; "Isolation oat alumina" should be --Isolation of a human seminal plasma...--;

"Glover Gene doning" should be --Glover, Gene Cloning--;

"Nagalla et al., Gastron-uleasy" should be --Nagalla et al., Gastrin-releasing Peptide--;

"Wasanwar, Enryl events" should be --Wassarman, Early Events... --;

Column 17, claim 10, line 67, replace "A cell into which..." with --A host cell into which...--.

Signed and Sealed this

Seventeenth Day of October, 1995

*Attest:*

BRUCE LEHMAN

*Attesting Officer*      *Commissioner of Patents and Trademarks*